United States Patent [19]

Myers

[11] Patent Number: 4,494,547
[45] Date of Patent: Jan. 22, 1985

[54] 2H-ISOINDOLEDIONES, THEIR SYNTHESIS AND USE AS RADIOSENSITIZERS

[75] Inventor: John A. Myers, Durham, N.C.

[73] Assignee: North Carolina Central University, Durham, N.C.

[21] Appl. No.: 248,793

[22] Filed: Mar. 30, 1981

[51] Int. Cl.³ .................... A61K 49/00; A61N 5/10
[52] U.S. Cl. ................................ 128/659; 424/1.1; 424/9; 548/427; 548/470
[58] Field of Search ............ 260/326.1; 128/659; 424/1.1, 9

[56] References Cited

U.S. PATENT DOCUMENTS 4,066,650  1/1978  Egyud ............................ 424/244
4,241,060  12/1980  Smithen ....................... 424/248.57

OTHER PUBLICATIONS

Radiation Sensitizers, Brady, Ed, Masson Publishing USA, Inc., pp. 497–501.
Meyers et al., J. Organic Chem. 45, (1980), 1202–1206.
Infante et al., Chem. Abstracts, 95; Abstract #18173e, (1981).
Infante et al., Rad. Res., 87: 480–481, (1981).
Dubois et al., J. Med. Chem., 21: 303–306, (1978).
Frankus et al., Chem. Abstracts, 85; Abstract #177259x, (1976).
Zhang, Chem. Abstracts, 96: Abstract #85795t, (1982).

*Primary Examiner*—Christine M. Nucker
*Attorney, Agent, or Firm*—Cushman, Darby & Cushman

[57] ABSTRACT

Isoindoledione compounds of the formula:

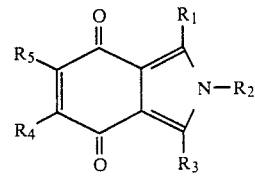

wherein:

$R_1$ and $R_3$ each separately is phenyl, substituted phenyl, alkyl of 1 to 4 carbons, —CHO, —CH$_2$OR$_6$, —CO$_2$R$_6$, —COR$_6$, hydrogen, or together with $R_2$ is a divalent alkyl or alkenyl group of 3 to 5 carbons which form a cyclic ring;

$R_2$ is phenyl, substituted phenyl, —CH$_2$OR$_6$, —CH$_2$CH$_2$OR$_6$, alkyl of 1 to 4 carbons or with either $R_1$ or $R_3$ is a divalent alkyl or alkenyl group of 3 to 5 carbons which form a cyclic ring;

$R_4$ and $R_5$ which may be the same or different each separately is hydrogen, alkyl of 1 to 4 carbons, —OR$_6$, —CO$_2$R$_6$, —COR$_6$, —CHO, —CH$_2$OR$_6$ or together $R_4$ and $R_5$ is a butadiene radical which forms a benzene ring;

$R_6$ is hydrogen or alkyl of 1 to 4 carbons; provided that $R_1$ and $R_3$ are not both phenyl and that when $R_4$ and $R_5$ are both hydrogen, $R_1$, $R_2$ and $R_3$ are not all methyl. The compounds are useful as radio-sensitizers in the therapeutic radiation of cancerous tissues.

19 Claims, 1 Drawing Figure

2H-ISOINDOLEDIONES, THEIR SYNTHESIS AND USE AS RADIOSENSITIZERS

BACKGROUND OF THE INVENTION

The synthesis of chemical compounds designed to selectively sensitize hypoxic cells in some tumors to the lethal effect of radiation has been the focus (See for example (a) K. C. Agrawal et al., *J. Med. Chem.*, 22, 583 (1979); (b) J. F. Fowler et al., *Cancer Treat. Rev.*, 3, 227 (1976); and (c) G. E. Adams et al., *Nature* (London) 239, 23 (1972).) of much research effort over the past several years. It has been observed that the ability of the radiosensitizing drugs to sensitize hypoxic cells is directly related to the electron affinity of the molecule. G. E. Adams and coworkers recently completed an impressive study of radiosensitization in hypoxic Chinese hamster cells in vitro by a series of nitroaromatic and nitroheterocyclic compounds (see, G. E. Adams et al., *Int. J. Radiat. Biol.*, 35, 133 (1979)). Among the conclusions they reached was the overwhelming importance of reduction potential to radiosensitization efficiency and the insensitivity to other, non-redox properties. The study also noted a failure to demonstrate any influence of solvent partition properties on radiosensitization efficiency or aerobic cytotoxicity of the compounds. For example, a 2-nitroimidazole, a 5-nitrofuran, a nitrobenzene and a quinone having virtually the same reduction potential were confirmed to have similar aerobic cytotoxicities. This lack of sensitivity to changes in molecular structure other than those which influence redox properties offers, according to the authors, an extraordinary flexibility in drug design. The most widely used radiosensitizers are the nitro derivatives, especially metronidazole and misonidazole. (See J. Martin Brown, *Radiat. Res.* 70, 469 (1977); G. E. Adams, *Int. J. Radiat. Oncol. Biol. Phys.*, 4, 135 (1978); and J. Denekamp and J. F. Fowler, *Int. J. Radiat. Oncol. Biol. Phys.*, 4, 168 (1978).) Some of these nitro compounds have already been used in radiochemical treatment of human subjects. However, recent investigations show that gastrointestinal toxicity with metronidazole and neurotoxicity with misonidazole limits the dosage of drug that can be administered. Some investigations claim that toxicity of the nitro derivatives arises when they are reduced to amines in the metabolic process.

The primary object of the present invention is to provide a new class of radiosensitizing agents which do not possess nitro groups.

It is a further object of the present invention to provide a new process for synthesizing the radiosensitizers of the present invention, namely, 2H-isoindoledniones.

These and other objects will become more apparent from the discussion which follows.

DETAILED DESCRIPTION OF THE INVENTION

The present invention provides for new isoindoledione compounds of the formula:

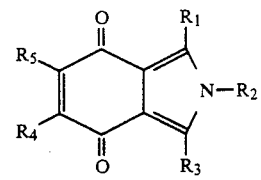

wherein:

$R_1$ and $R_3$ each separately is phenyl, substituted phenyl, alkyl of 1 to 4 carbons, —CHO, —CH$_2$OR$_6$, —CO$_2$R$_6$, —COR$_6$, hydrogen, or together with $R_2$ is a divalent alkyl or alkenyl group of 3 to 5 carbons which form a cyclic ring;

$R_2$ is phenyl, substituted phenyl, —CH$_2$OR$_6$, —CH$_2$CH$_2$OR$_6$, alkyl of 1 to 4 carbons or with either $R_1$ or $R_3$ is a divalent alkyl or alkenyl group of 3 to 5 carbons which form a cyclic ring;

$R_4$ and $R_5$ which may be the same or different each separately is hydrogen, alkyl of 1 to 4 carbons, —OR$_6$, —CO$_2$R$_6$, —COR$_6$, —CHO, —CH$_2$OR$_6$ or together $R_4$ and $R_5$ is a butadiene radical which forms a benzene ring;

$R_6$ is hydrogen or alkyl of 1 to 4 carbons; provided that $R_1$ and $R_3$ are not both phenyl and that when $R_4$ and $R_5$ are both hydrogen, $R_1$, $R_2$ and $R_3$ are not all methyl.

Preferred are the isoindoledione compounds wherein $R_1$ and $R_3$ are selected from phenyl alkyl of 1 to 4 carbons and together with $R_2$, $R_1$ or $R_3$ forms a cyclic ring;

$R_4$ and $R_5$ which may be the same or different are selected from hydrogen, alkyl of 1 to 4 carbons, and methoxy.

As an example of but a few compounds provided for herein, there is included:

1,2-dimethyl-3-phenyl-2H-benz[f]isoindole-4,9-dione;
1-phenyl-2,3-trimethylene-2H-benz[f]isoindole-4,9-dione;
1,2,5-trimethyl-3-phenyl-2H-isoindole-4,7-dione;
1,2,6-trimethyl-3-phenyl-2H-isoindole-4,7-dione;
5-methoxy-1,2,6-trimethyl-3-phenyl-2H-isoindole-4,7-dione;
6-methoxy-1,2,5-trimethyl-3-phenyl-2H-isoindole-4,7-dione;
5-methyl-1-phenyl-2,3-trimethylene-2H-isoindole-4,7-dione;
6-methyl-1-phenyl-2,3-trimethylene-2H-isoindole-4,7-dione;
5-methoxy-6-methyl-3-phenyl-1,2-trimethylene-2H-isoindole-4,7-dione;
6-methoxy-5-methyl-3-phenyl-1,2-trimethylene-2H-isoindole-4,7-dione;
1-methyl-2,3-trimethylene-2H-benz[f]isoindole-4,9-dione;
2-methyl-1-phenyl-2H-benz[f]isoindole-4,9-dione;
2,5-dimethyl-1-phenyl-2H-isoindole-4,7-dione;
2,6-dimethyl-1-phenyl-2H-isoindole-4,7-dione;
1,5-dimethyl-2,3-trimethylene-2H-isoindole-4,7-dione;
1,6-dimethyl-2,3-trimethylene-2H-isoindole-4,7-dione;
1-carboethoxy-5-methyl-2,3-trimethylene-2H-isoindole-4,7-dione;
1-carboethoxy-6-methyl-2,3-trimethylene-2H-isoindole-4,7-dione;
1-carboethoxy-2,5-dimethyl-3-phenyl-2H-isoindole-4,7-dione;

1-carboethoxy-2,6-dimethyl-3-phenyl-2H-isoindole-4,7-dione;
5-methyl-1,2-trimethylene-2H-isoindole-4,7-dione;
6-methyl-1,2-trimethylene-2H-isoindole-4,7-dione; and
1,2,3,5-tetramethyl-2H-isoindole-4,7-dione.

One other aspect of the present invention is directed to a process for the production of 2H-isoindolediones by the 1,3-dipolar addition of oxazolium 5-oxides to 1,4-quinones. This process is generally described in a paper prepared by myself and colleagues titled "Synthesis of 2H-Isoindole-4,7-diones by 1,3-Dipolar Addition of Oxazolium 5-Oxides to 1,4-Quinones", *J. Org. Chem.*, 45, 1202 (1980), the entire contents of which are incorporated herein by reference.

Two methods are known for the synthesis of certain specific 2H-isoindole-4,7-diones and include photolysis of 2,3-diphenyl-2H-azirine in the presence of 1,4-quinones (Gilgen et al., *Helv. Chim. Acta.*, 57, 2634 (1974)) and zinc-induced intramolecular cyclization of 1,2,5-trimethyl-3,4-bis(bromoacetyl)pyrrole followed by dehydrogenation (Ghera et al., *J. Chem. Soc. Chem. Commun.* 1034 (1974)). However, no utility was specified for these specific compounds.

The method of the present invention provides a general and more convenient process for the preparation of this heterocyclic quinone system from N-acyl amino acids and 1,4-quinones, which are readily available starting materials.

The invention thus provides a method for the preparation of 2H-isoindolediones by the 1,3-dipolar addition of oxazolium 5-oxides to 1,4-quinones which comprises the steps of:

(a) generating at a temperature of from about 20° to about 80° C. in the presence of a non-polar aprotic solvent and a dehydration agent, an oxazolium 5-oxide of the formula:

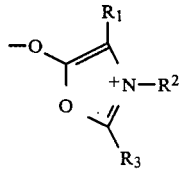

from an N-acyl amino acid of the formula

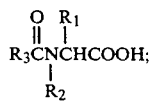

(b) reacting the oxazolium 5-oxide obtained in step (a) with a 1,4-quinone of the formula

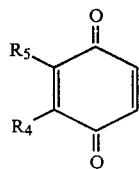

in the presence of a non-polar aprotic solvent for a period of time sufficient to produce a product of the formula

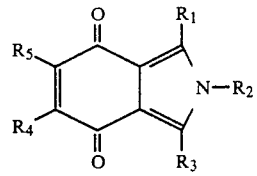

wherein:

$R_1$ and $R_3$ each separately is phenyl, substituted phenyl, alkyl of 1 to 4 carbons, —CHO, —CH$_2$OR$_6$, —CO$_2$R$_6$, —COR$_6$, hydrogen, or together with R$_2$ are a divalent alkyl or alkenyl group of 3 to 5 carbons which form a cyclic ring;

$R_2$ is phenyl, substituted phenyl, —CH$_2$OR$_6$, —CH$_2$CH$_2$OR$_6$, alkyl of 1 to 4 carbons or with either R$_1$ or R$_3$ is a divalent alkyl or alkenyl group of 3 to 5 carbons which form a cyclic ring;

$R_4$ and $R_5$ which may be the same or different is hydrogen, alkyl of 1 to 4 carbons, —OR$_6$, —CO$_2$R$_6$, —COR$_6$, —CHO, —CH$_2$OR$_6$ or together R$_4$ and R$_5$ are a butadiene radical which form a benzene ring;

$R_6$ is hydrogen or alkyl of 1 to 4 carbons; and (c) separating and recovering the product from the solvent solution.

The dehydration agent is preferably acetic anhydride or dicyclohexyl-carbodiimide. For enhanced yields, the generation and reaction steps should be carried out in an inert atmosphere, e.g., nitrogen or argon.

The dehydration agent is necessary to remove water from the N-acylamino acid. When one uses acetic anhydride, acetic acid is formed. Thus, when the agent is acetic anhydride, prior to step (b) the reaction solution is neutralized by the addition of sodium carbonate and sodium sulfate.

Preferred reactants include those wherein the 1,4-quinone is selected from the group consisting of 1,4-benzoquinone; 1,4-naphthoquinone; 2-methyl-1,4-benzoquinone and 2-methyl-3-methoxy-1,4-benzoquinone, and the oxazolium 5-oxide is selected from the group consisting of 3-methyl-2,4-diphenyloxazolium-5-oxide; 2,3-dimethyl-4-phenyloxazolium-5-oxide; 2-phenyl-3,4-trimethyleneoxazolium-5-oxide and 2-methyl-3,4-trimethylene-oxazlium-5-oxide.

The amounts of reactants used is not critical, but preferably equimolar amounts 1,4-quinone and oxazolium 5-oxide are used.

It will be appreciated from the discussion below, that while reference is made to specific compounds, the method is applicable to the genus noted above.

As used herein, the term "substituted phenyl" is defined as phenyl bearing at least one alkyl of 1 to 4 carbons, alkoxy of 1 to 4 carbons, —OR$_6$, —COR$_6$, or mixtures thereof where R$_6$ is as defined.

Synthesis of the 5-methyl-2H-isoindole-4,7-diones in moderate yields was accomplished by the reaction of an oxazolium 5-oxide with 2-methyl-1,4-benzoquinone in an aprotic solvent under nitrogen. The particular oxazolium 5-oxide was generated in solution from its N-acyl-N-alkyl amino acid precursor by reaction with acetic anhydride or dicyclohexylcarbodiimide. The well-established 1,3-dipolar addition of 2 to the unsubstituted C═C of 4c is followed by carbon dioxide expulsion and oxidation to give the isoindolequinones 1 (see Scheme I below). Structural assignments for 1 were based on the NMR, IR, and mass spectral data.

SCHEME I

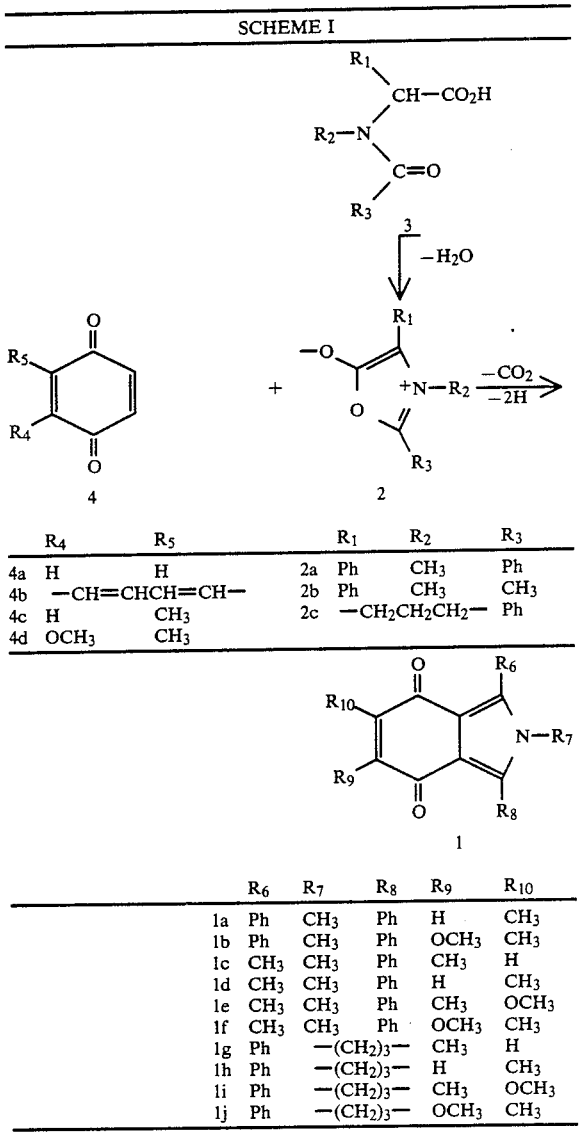

| | $R_4$ | $R_5$ | | $R_1$ | $R_2$ | $R_3$ |
|---|---|---|---|---|---|---|
| 4a | H | H | 2a | Ph | $CH_3$ | Ph |
| 4b | —CH=CHCH=CH— | | 2b | Ph | $CH_3$ | $CH_3$ |
| 4c | H | $CH_3$ | 2c | —$CH_2CH_2CH_2$— | | Ph |
| 4d | $OCH_3$ | $CH_3$ | | | | |

| | $R_6$ | $R_7$ | $R_8$ | $R_9$ | $R_{10}$ |
|---|---|---|---|---|---|
| 1a | Ph | $CH_3$ | Ph | H | $CH_3$ |
| 1b | Ph | $CH_3$ | Ph | $OCH_3$ | $CH_3$ |
| 1c | $CH_3$ | $CH_3$ | Ph | $CH_3$ | H |
| 1d | $CH_3$ | $CH_3$ | Ph | H | $CH_3$ |
| 1e | $CH_3$ | $CH_3$ | Ph | $CH_3$ | $OCH_3$ |
| 1f | $CH_3$ | $CH_3$ | Ph | $OCH_3$ | $CH_3$ |
| 1g | Ph | —$(CH_2)_3$— | | $CH_3$ | H |
| 1h | Ph | —$(CH_2)_3$— | | H | $CH_3$ |
| 1i | Ph | —$(CH_2)_3$— | | $CH_3$ | $OCH_3$ |
| 1j | Ph | —$(CH_2)_3$— | | $OCH_3$ | $CH_3$ |

Cycloaddition of the unsymmetrical oxazolium 5-oxide 2b or 2c to 4c occurred in a non-regiospecific manner giving a mixture of two isomers in each case. For example, reaction of 2,3-dimethyl-4-phenyloxazolium 5-oxide (2b), formed by treatment of N-methyl-N-acetyl-C-phenylglycine (3b) with an equimolar amount of acetic anhydride at reflux in tetrahydrofuran, with 4c gave a mixture of 1,2,5-trimethyl- and 1,2,6-trimethyl-3-phenyl-2H-isoindole-4,7-diones (1c and 1d). The presence of two distinct doublets for the quinone methyl hydrogens at δ 1.98 and 2.04, overlapping quartets for the quinone vinylic hydrogens at δ 6.43 and 6.50, and two singlets for the pyrrole methyl hydrogens at δ 2.62 and 2.64 in the NMR spectrum provides evidence of these two structural isomers. In a similar manner, reaction of 2c, generated from N-benzolyproline (3c), with 4c gave a mixture of 1g and 1h. The NMR spectrum revealed overlapping doublets at δ 2.03 and 2.05 for the quinone methyl hydrogens and overlapping quartets at δ 6.49 and 6.52 for the quinone vinylic hydrogens. The "trimethylene" portion of 1g and 1h appeared as two broadened triplets and a broadened patent.

The invention in its further aspect embodies the use of 2H-isoindolediones as radiosensitizers for the radiotherapeutic treatment of cancerous tissues.

The radiosensitizing compositions for use in the radiotherapeutic treatment of cancerous tissues according to the present invention comprises as an active ingredient an isoindoledlone compound of the formula

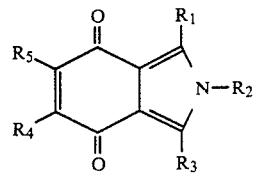

wherein:

$R_1$ and $R_3$ each separately is phenyl, substituted phenyl, alkyl of 1 to 4 carbons, —CHO, —$CH_2OR_6$, —$CO_2R_6$, —$COR_6$, hydrogen, or together with $R_2$ is a divalent alkyl or alkenyl group of 3 to 5 carbons which form a cyclic ring;

$R_2$ is phenyl, substituted phenyl, —$CH_2OR_6$, —$CH_2CH_2OR_6$, alkyl of 1 to 4 carbons or with either $R_1$ or $R_3$ is a divalent alkyl or alkenyl group of 3 to 5 carbons which form a cyclic ring;

$R_4$ and $R_5$ which may be the same or different each separately is hydrogen, alkyl of 1 to 4 carbons, —$OR_6$, —$CO_2R_6$, —$COR_6$, —CHO, —$CH_2OR_6$ or together $R_4$ and $R_5$ is a butadiene radical which forms a benzene ring;

$R_6$ is hydrogen or alkyl of 1 to 4 carbons; together with a pharmaceutically acceptable carrier.

Suitably, the composition is in the form of an injectable composition wherein the pharmaceutically acceptable carrier is selected from the group consisting of sterile buffered saline solution and sterile water.

The composition may also be in the form of a tablet, capsule, syrup or elixir, if desired.

The invention further provides for a method for the radiotherapeutic treatment of cancerous tissues in mammals which comprises:

(a) administering to said mammal, in an amount effective to enhance subsequent radiation of cancerous tissue, a radiosensitizing composition as defined above; and (b) subsequently exposing the cancerous tissue to radiation whereby enhanced radiation of the tissue is achieved.

The amount of said composition which is administered generally ranges from about 0.1 to 0.8 mg of active ingredient per kg body weight of the mammal and preferably is about 0.4 mg per kg of body weight. The most common form of radiation used is gamma radiation.

Generally, the time between steps (a) and (b) is from between about 15 to about 60 minutes and sufficient to permit the active ingredient to reach the locus of the cancerous tissue.

Figure 1:
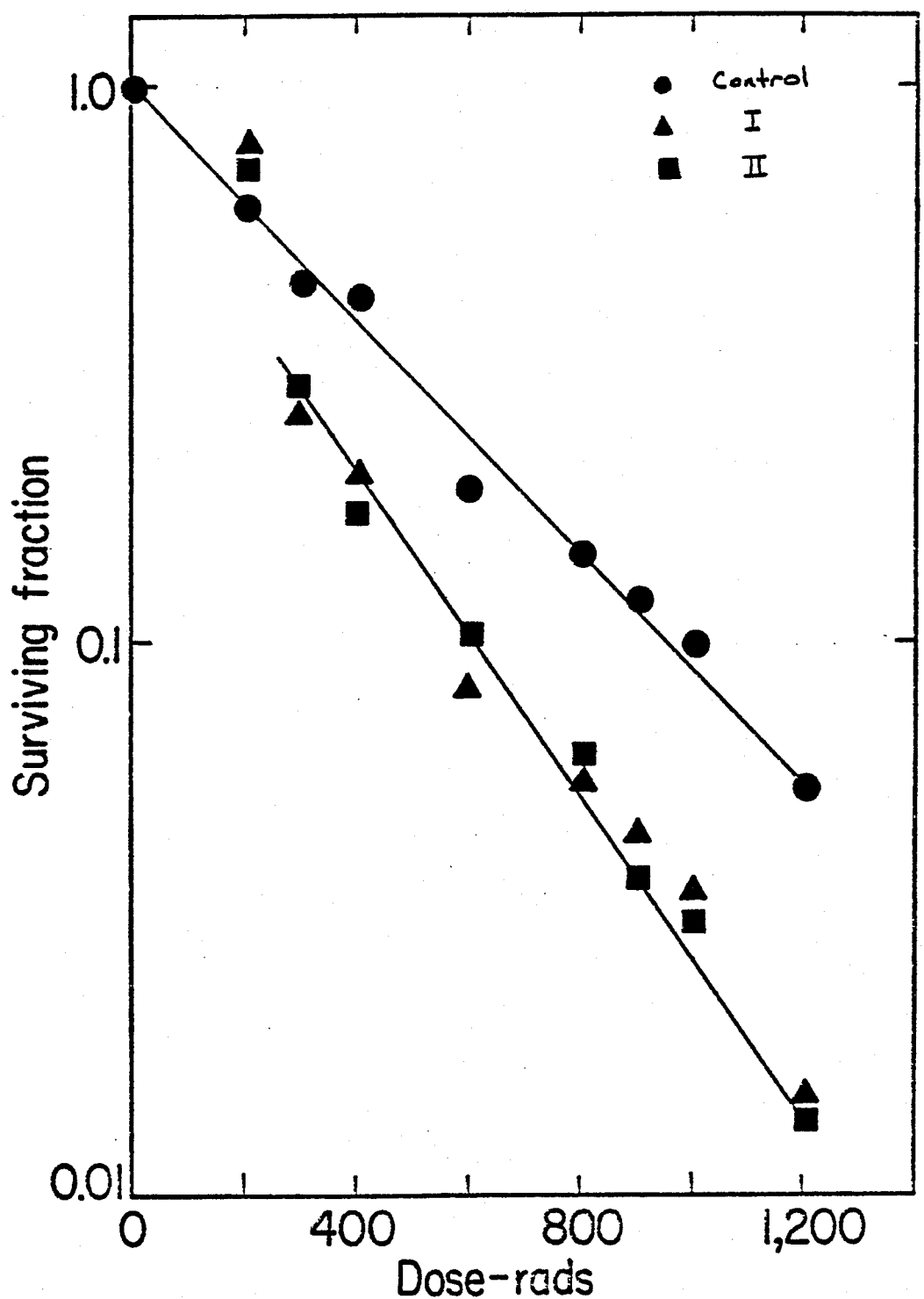
FIG. 1 is a graph representing the effect of isoindole-4,7-diones in soft tissue sarcoma transplanted mice: (●) control (cancer cells irradiated without radiosensitizer); (▶) 0.4 μg/g 1,2,5-and 1,2,6-trimethyl-3-phenyl-2H-isoindole-4,7-dione; (■) 0.4 μg/g 5- and 6-methyl-1-phenyl-2,3-trimethylene-2H-isoindole-4,7-diones.

The following data is offered to more fully illustrate the present invention, but is not to be construed as limiting the scope thereof. In the data given, the structural formulas are presented in Schemes 1 and 2.

SCHEME 2

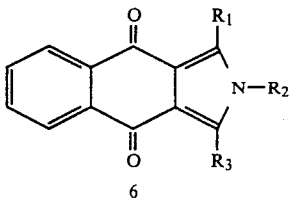

| | $R_1$ | $R_2$ | $R_3$ |
|---|---|---|---|
| 6a | Ph | $CH_3$ | Ph |
| 6b | Ph | $CH_3$ | $CH_3$ |
| 6c | | —$CH_2CH_2CH_2$— | Ph |

EXAMPLE ONE 2,5-Dimethyl-1,3-diphenyl-2H-isoindole-4,7-dione (1a)

To a suspension of 5.38 g (0.020 mol) of N-methyl-N-benzoyl-C-phenylglycine (3a) in 50 mL of dry THF was added 2 mL (0.020 mol) of $Ac_2O$. The white suspension was maintained at 55°–60° C. with stirring for 30 min., or until a yellow solution of 2a was observed. One gram each of $Na_2SO_4$ and $Na_2CO_3$ were added, and the mixture was stirred for an additional 10 min. Twenty millimoles (2.44 g) of 2-methyl-1,4-benzoquinone (4c) was added, and the mixture was stirred for 3 h at room temperature. The yellow-orange mixture was filtered, and the precipitate, presumably salts, was washed twice with 30 mL portions of $CH_2Cl_2$. The organic layers were combined and concentrated under reduced pressure to a gummy yellow paste. Treatment of the residue with 20 mL of $CH_3CN$ afforded 1.0 g of yellow-orange solid. The filtrate was concentrated to a dark red oil, which was treated with 2-propanol and water to give 1.70 g of yellow-orange solid in two crops. The crude solids were combined and recrystallized from 2-propanol to afford 2.45 g (37%) of orange solid: mp 172°–174° C.; IR 1640 (C=O) cm$^{-1}$; NMR (CDCl$_3$) $\delta$2.02 (d, J=1.5 Hz, 3, quinone CH$_3$), 3.32 (s, 3, NCH$_3$) 6.51 (q, J=1.5 Hz, 1, quinone H) and 7.53 (s, 10, ArH); MS m/e 327 (M+). Anal. (C$_{22}$H$_{17}$NO$_2$) C, H, N.

EXAMPLE TWO

Mixture of 1,2,5-trimethyl- and 1,2,6-trimethyl-3-phenyl-2H-isoindole-4,7-diones (1c and 1d)

Using 4.14 g (0.020 mol) of N-methyl-N-acetyl-C-phenylglycine (3b) in place of 3a, the same procedure with $Ac_2O$ and 4c was followed yielding from 2-propanol 1.74 g (33%) of bright yellow-orange solid: mp 196°–198° C.; IR 1645 (C=O) cm$^{-1}$; NMR (CDCl$_3$) $\delta$1.98 and 2.04 (two d, J=1.8 Hz, 3, quinone CH$_3$), 2.62 and 2.64 (two s, 3, pyrrole CH$_3$), 3.39 (5, 3, NCH$_3$), 6.43 and 6.50 (two q, J=1.8 Hz, 1, quinone H), 7.44 (br s, 5, ArH); MS m/e 265 (M+). Anal. (C$_{17}$H$_{15}$NO$_2$) C, H, N.

EXAMPLE THREE

Mixture of 5-methyl- and 6-methyl-1-phenyl-2,3-trimethylene-2H-isoindole-4,7-diones (1g and 1h)

A suspension of 2.19 g (0.010 mol) of N-benzoylproline (3c) in 3 mL of $Ac_2O$ was heated until the white solid dissolved giving a yellow orange solution of 2c. Forty mL of benzene was added to the solution followed by 0.5 g each of $Na_2CO_3$ and $Na_2SO_4$. After stirring 10 min., 1.22 g (0.010 mol) of 4c was added, and the mixture was refluxed for 2 hours. After cooling, a white solid was removed by filtration. Evaporation of the filtrate left an orange-brown residue. Recrystallization from 2-propanol and water yielded 0.78 g (28%) of bright orange crystals: mp 178°–179° C.; IR 1640 cm$^{-1}$; NMR (CDCl$_3$) $\delta$2.03 and 2.05 (overlapping d, J=1.5 Hz, 3, quinone CH$_3$) 2.52 (apparent p, J=7 Hz, 2, —CH$_2$CH$_2$CH$_2$—), 3.13 (t, J=7 Hz, 2, pyrrole CH$_2$), 3.98 (t, J=7 Hz, 2, NCH$_2$), 6.49 and 6.52 (overlapping g, J=1.5 Hz, 1, quinone H), 7.25–7.70 (complex m, 5, ArH); MS m/e 277 (M+). Anal. (C$_{18}$H$_{15}$NO$_2$) C, H, N.

EXAMPLE FOUR

1-Phenyl-2,3-trimethylene-2H-benz[f]isoindole-4,9-dione (6c)

N-benzoylproline (2.2 g, 0.010 mol) was heated in 3 mL of acetic anhydride until a slightly yellow solution was obtained. Benzene (40 mL) was added to the solution followed by 0.5 g of $Na_2CO_3$ and 0.5 g of $Na_2SO_4$. 1,4-Naphthoquinone (1.69 g, 0.010 mol) was added, and the mixture was heated under reflux for 2.5 hours. Upon standing overnight, the mixture solidified. A brown solid containing bright yellow crystals was collected by filtration. The solid was triturated in warm benzene, and the resulting suspension was filtered. Beige crystals began forming in the filtrate as it cooled. When yellow crystals began to separate, the liquid portion was quickly decanted into another flask. Yellow crystals, 1.25 g (42%), were separated from the liquid and were collected by filtration. An analytical sample was obtained after several recrystallizations from benzene: mp 226°–228° C. (dec.); IR 1645 (C=O) cm$^{-1}$; H-1 NMR (CDCl$_3$) $\delta$2.60 (p, J=7 Hz, 2, —CH$_2$CH$_2$CH$_2$—), 3.27 (t, J=7 Hz, 2, pyrrole CH$_2$), 4.04 (t, J=7 Hz, 2, NCH$_2$), 7.35–7.80 (complex m, 7, ArH), 8.10–8.35 (m, 2, ArH), MS m/e (rel. intensity) 314 (23), 313 (100) M+, 312 (40). Anal. Calcd for C$_{21}$H$_{15}$NO$_2$: m/e 313.1102. Found: m/e 313.1106. Anal. Calcd for C$_{21}$H$_{15}$NO$_2$: C, 80.49; H, 4.83; N, 4.47. Found: C, 80.43; H, 4.68; N, 4.22.

EXAMPLE FIVE

1-Methyl-2,3-trimethylene-2H-benz[f]isoindole-4,9-dione (6d)

L-proline (1.15 g, 0.010 mole) was heated in 5 mL of acetic anhydride until a yellow solution was obtained. Toluene (10 mL) and 1,4-naphthoquinone (1.60 g, 0.010 mol) were added to the solution. Heating was continued for 1.5 hours. After standing overnight, 1.16 g (46%) of a brown solid was filtered from the reaction mixture. This solid was recrystallized several times from ethanol to give bright yellow crystals: mp 212°–216° C.; IR 1660 (C=O) cm$^{-1}$; H-1 NMR (CDCl$_3$) $\delta$2.35–2.85 (s and m, 5, pyrrole CH$_3$ and CH$_2$CH$_2$CH$_2$), 3.10 (t, J=7 Hz, 2, pyrrole CH$_2$), 3.82 (t, J=7 Hz, 2, NCH$_2$), 7.45–7.90 (complex m, 2, ArH), 8.05–8.40 (complex m, 2, ArH);

Anal. Calcd for C$_{16}$H$_{13}$NO$_2$: C, 76.48; H, 5.21; N, 5.57. Found: C, 76.51; H, 4.96; N, 5.42.

EXAMPLE SIX 1,2-Simethyl-3-phenyl-2H-benz[f]isoindole-4,9-dione (6b)

To a suspension of 4.14 g (0.020 mol) of N-methyl-N-acetyl-C-phenylglycine in 50 mL of methylene chloride was added 4.12 g (0.020 mol) of N,N'-dicyclohexylcarbodiimide (DCC) with stirring. The mixture was heated under reflux for 45 minutes. White solid N,N'-dicyclohexylurea (DCU) was separated by filtration and washed with small portions of fresh solvent. To the yellow-orange filtrate was added 3.16 g (0.020 mol) of 1,4-naphthoquinone, and the dark mixture was heated under reflux for two hours. Evaporation of the solvent left a dark residue, which was taken up in methylene chloride and filtered from a grey solid, presumably more DCU. Evaporation of the solvent and crystallization of the residue from 2-propanol gave 0.62 g (10%) of yellow-green crystals, mp 242°–245° C. Recrystallization from 2-propanol gave yellow crystals: mp 242°–243.5° C.; IR 1655 and 1645 (C=O) cm$^{-1}$; H-1 NMR (CDCl$_3$) δ2.75 (s, 3, pyrrole CH$_3$), 3.43 (s, 3, NCH$_3$), 7.15–8.50 (m, 9, ArH); MS m/e (rel. intensity) 302 (22), 301 (100) M+, 300 (82). Anal. Calcd for C$_{20}$H$_{15}$NO$_2$: m/e 301.1102. Found: m/e 301.1105. Anal. Calcd for C$_{20}$H$_{15}$NO$_2$: C, 79.71; H, 5.02; N, 4.65. Found: C, 79.68; H, 4.93; N, 4.34.

EXAMPLE SEVEN

2-Methyl-1-phenyl-2H-benz[f]isoindole-4,9-dione (6e)

N-Benzoylsarcosine (3.86 g, 0.020 mol) was dissolved in 7 mL (0.070 mol) of acetic anhydride and heated until a yellow color was observed. Forty milliliters of toluene was added to the reaction flask after the color change was observed. After stirring for 15 minutes, 3.16 g (0.020 mol) of 1,4-naphthoquinone was added. The resulting black mixture was heated for 1.5 hours, then stirred at room temperature overnight. The mixture was filtered to yield 1.13 g (19%) of yellow-brown solid. The solid was recrystallized several times from toluene to give bright yellow crystals: mp 268°–271° C.; IR 1655 and 1645 (C=O) cm$^{-1}$; H-1 NMR (CDCl$_3$) δ 3.60 (s, 3, NCH$_3$), 7.10–7.75 (complex m and s, 8, ArH and pyrrole H), 7.95–8.30 (m, 2, ArH); MS m/e 287 M+.

EXAMPLE EIGHT

Mixture of 5-methyl- and 6-methyl-1-phenyl-2,3-trimethylene-2H-isoindole-4,9-diones (1g and 1h)

N-benzoylproline (2.2 g, 0.010 mol) was heated in 3 mL of acetic anhydride until a slightly yellow solution was obtained. Benzene (40 mL) was added to the solution followed by 0.5 g of Na$_2$CO$_3$ and 0.5 g of Na$_2$SO$_4$. 2-methyl-1,4-benzoquinone (1.22 g, 0.010 mol) was added, and the mixture was heated under reflux for 2 hours. After cooling, an orange solid was separated by filtration and recrystallized from 2-propanol and water. A bright orange solid, 0.78 g (28%) was collected; mp 178°–179° C.; IR 1640 (C=O) cm$^{-1}$; H-1 NMR (CDCl$_3$) δ 2.03 and 2.05 (overlapping d, J=1.5 Hz, 3, quinone CH$_3$), 2.52 (apparent p, J=7 Hz, 2, —CH$_2$CH$_2$CH$_2$—), 3.13 (t, J=7 Hz, 2, pyrrole CH$_2$), 3.98 (t, J=7 Hz, 2, NCH$_2$), 6.49 and 6.52 (overlapping q, J=1.5 Hz, 1, quinone H), 7.25–7.70 (complex m, 5, ArH); MS m/e (rel. intensity) 278 (20), 277 (100) M+, 276 (54). Anal. calcd for C$_{18}$H$_{15}$NO$_2$: m/e 277/1103. Found: m/e 277.1107. Anal calcd for C$_{18}$H$_{15}$NO$_2$: C, 77.96; H, 5.45; N, 5.05. Found: C, 78.04; H, 5.17; N, 4.81.

EXAMPLE NINE

Mixture of 1,5-dimethyl- and 1,6-dimethyl-2,3-trimethylene-2H-isoindole-4,7-diones (1k and 1l)

A suspension of 3.46 g (0.030 mol) of L-proline in 15 mL of acetic anhydride was heated to reflux until the white solid dissolved and a pale orange color developed. A solution of 3.66 g (0.030 mol) of 2-methyl-1,4-benzoquinone in 80 ml of toluene was added. After stirring at reflux for 2.5h, the mixture was evaporated under reduced pressure. The residue was redissolved in 15 ml of methylene chloride. Petroleum ether was added until the dark brown solution separated into two layers. A yellow solution was decanted from a dark brown oil. As more petroleum ether was added to the yellow solution, more oil separated. When yellow solid first appeared in the yellow solution as petroleum ether was being added, the suspension was quickly decanted into another flask. More petroleum ether was added, and the mixture was cooled at 0° C. overnight. Bright yellow crystals, 0.40 g (6%) were collected: mp 149°–151° C.; IR 1640 (C=O) cm$^{-1}$; NMR (CDCl$_3$) δ 2.01 (d, J=1.5 Hz, 3, quinone CH$_3$), 2.48 (s, 3, pyrrole CH$_3$), 2.58 (p, J=6 Hz, 2, —CH$_2$CH$_2$CH$_2$—), 3.05 (t, J=6 Hz, 2, pyrrole CH$_2$), 3.88 (t, J=6 Hz, 2, NCH$_2$), 6.39 (q, J=1.5 Hz, 1, quinone H). MS m/e (rel. intensity) 216 (15), 215 (100) M+, 214 (81). Anal. Calcd for C$_{13}$H$_{13}$NO$_2$: m/e 215.0946. Found: m/e 215.0943. Anal. Calcd for C$_{13}$H$_{13}$NO$_2$: C, 72.55; H, 6.09; N, 6.51. Found: C, 72.40; H, 6.10; N, 6.28.

EXAMPLE TEN

Mixture of 2,5-dimethyl- and 2,6-dimethyl-1-phenyl-2H-isoindole-4,7-diones (1m and 1n)

A suspension of 7.72 g (0.040 mol) of N-benzoylsarcosine in 16 mL of acetic anhydride was heated until the white solid dissolved giving a yellow-orange solution. A gram of sodium carbonate was added, and the mixture was stirred for 15 min. A solution of 4.88 g (0.040 mol) of 2-methyl-1,4-benzoquinone in 80 mL of toluene was added. The resulting mixture was refluxed for 2.5h. After cooling, a white solid was removed by filtration. Evaporation of the filtrate left a red-brown oil which was redissolved in 15 mL of methylene chloride. Twenty milliliters of petroleum ether was added, and the solution was cooled to 0° for two days. A yield of 0.93 g (9%) of bright orange crystals was separated by filtration: mp 177°–179° C.; IR 1630 (C=O) cm$^{-1}$; NMR (CDCl$_3$) δ 2.03 and 2.07 (2, d, J=1.6 Hz, 3, quinone CH$_3$), 3.56 (s, 3, NCH$_3$), 6.4–6.7 (overlapping q, J=1.6 Hz, 1, quinone H), 7.31 (s, 1, pyrrole H), 7.50 (s, 5, ArH); MS m/e (rel. intensity) 252 (17), 251 (100) M+, 250 (92). Anal. Calcd for C$_{16}$H$_{13}$NO$_2$: m/e 251.0945. Found: m/e 251.0948.

Pulse Radiolysis Experiments

The pulse radiolysis experiments were carried out with a computer-controlled apparatus. Electron pulses from an ARCO LP-7 linear accelerator were of 5–50 ns duration and provided 0.1 to 1 krad per pulse. Dosimetry was done with N$_2$O saturated SCN$^-$ solutions.

In order to determine the one-electron reduction potentials of the isoindolediones, 9,10-anthraquinone-2- sulfonate was used as a reference. The kinetics of electron transfer and the equilibrium constants were used to derive the redox potentials given in Table I along with values determined previously for representative quinone and nitroimidazole radiosensitizers. It is seen from Table I that the electron affinities of the isoindoledionesunder study fall between those of known radiosensitizers. Therefore, it is expected that the isoindolediones may act as efficient radiosensitizers.

TABLE I

ONE-ELECTRON REDOX POTENTIAL OF VARIOUS RADIOSENSITIZERS

| Compound | Redox Potential (mV) |
|---|---|
| I (1c + 1d) | −423[a] |
| II (1g + 1h) | −427[a] |
| IV[e] | −438[a] |
| Menadione | −203[b] |
| Duroquinone | −235[b] |
| Misonidazole | −380[c,d] |
| Metronidazole | −486[c] |

[a]Determined from the equilibrium constants in Table I using a redox potential of −380 mV for AQS as reference.
[b]From D. Meisel and G. Czapski, One-electron transfer equilibria and redox potentials of radicals studied by pulse radiolysis, J. Phys. Chem., 79, 1503–1509 (1975).
[c]G. E. Adams, I. R. Flockhart, C. E. Smithen, I. J. Stratford, P. Wardman and M. E. Watts, Electron affinic sensitization. VIII. A correlation between structures, one electron reduction potentials and efficiencies of nitroimidazoles as hypoxic cell radiosensitizers. Radiat. Res. 67, 9–20 (1976).
[d]D. Meisel and P. Neta, One-electron redox potentials of nitro compounds and radiosensitizers. Correlation with spin densities of their radical anions. J. Am. Chem. Soc. 97, 5198–5203 (1975).
[e]1,5-dimethyl and 1,6-dimethyl-2,3-trimethylene-2H—isoindole-4,7-diones.

In Vivo Experiments

Mice: The mice used throughout these studies were female Balb-c from a production colony. Mice were housed six per cage with food and water.

Tumor: Connective tissue sarcoma resembling chondrosarcoma was used in this study. Injections were made intravenously using $5 \times 10^5$ viable cells (trypan blue exclusion test) in 0.1 mL with cells harvested from the 150th through 164th in vitro passages.

Long Colony Assay: Balc-c mice bearing soft tissue sarcoma ca. 600 mm$^3$ were injected intraperitoneal with different dosages (0.1–0.4 μg/g) of isoindole-4,7-diones 30 minutes before irradiation with various doses from a Co-60 gamma source. Immediately after irradiation single cell suspensions were prepared and tumor cells ($5 \times 10^5$) were injected intravenously to healthy mice. After six weeks, a quantitative assay of tumor nodules in mice lungs is carried out and survival parameters are determined and are given in Tables II and III.

TABLE II

RADIOSENSITIZATION EFFECTS ON LUNG COLONY ASSAY[a]

| Radiosensitizer | Concentration (μg/g) | Irradiation Dose (rads) | Nodules |
|---|---|---|---|
| None | 0 | 0 | 78 |
| None | 0 | 800 | 36 |
| I (1c + 1d) | 0.4 | 0 | 68 |
| I (1c + 1d) | 0.1 | 800 | 27 |
| I (1c + 1d) | 0.2 | 800 | 17 |
| I (1c + 1d) | 0.4 | 800 | 8 |
| II (1g + 1h) | 0.4 | 0 | 67 |
| II (1g + 1h) | 0.1 | 800 | 29 |
| II (1g + 1h) | 0.2 | 800 | 18 |
| II (1g + 1h) | 0.4 | 800 | 8 |
| Menadione | 0.4 | 0 | 56 |
| Menadione | 0.2 | 800 | 32 |
| Menadione | 0.2 | 800 | 24 |
| Menadione | 0.4 | 800 | 17 |
| Misonidazole | 0.4 | 0 | 64 |
| Misonidazole | 0.1 | 800 | 7 |
| Misonidazole | 0.4 | 800 | 3 |

[a]Average value of at least three experiments. Twelve mice in each experiment. Standard deviation = 4.0, standard error = 1.6

Table II shows the results of experiments using different doses of the sensitizers I and II and a constant irradiation dose of 800 rads. The number of nodules in the lungs decreases from 36 in control (without sensitizer) to 8 at the highest sensitizer concentration. A nonirradiated control with the highest drug concentration gives a value of 68. Results for menadione and misonidazole are also given for comparison. It is clear from Table III that the isoindole-4,7-diones inhibit cancer metastasis to a greater extent than menadione but to a lesser extent than misonidazole.

Similar procedures were carried out at different irradiation doses (200–1200 rads) using the higher concentrations of the isoindole-4,7-diones I (1c+1d) mixture, II (1g+1h) mixture) and IV (mixture of 1,5-dimethyl and 1,6-dimethyl-2,3-trimethylene-2H-isoindole-4,7-diones).

Using the lung colony assay technique, survival curves (shown in FIG. 1) were constructed by plotting N/No (number of lung nodules in the radiosensitizer treated mice per number of lung nodules in the untreated mice) vs. the radiation dose from 200 to 1,400 at 200 rad intervals. The radiation dose necessary to kill 37% of the cancerous cells (Do) was determined from the plot. The Do values and the corresponding modifying factors are presented in Table III. Do for the control was 420±20 rads and for the isoindole-4,7-diones was about 320±20 rads in all cases, showing a modifying factor of about 1.3 which compares favorably with menadione's modifying factor of 1.17. As the irradiation dose is increased, a higher modifying factor between the control and the isoindole-4,7-diones can be observed. This fact is an important characteristic of any radiosensitizing agent.

TABLE III

RADIOSENSITIZATION EFFECTS ON LUNG COLONY ASSAY[a]

| Radiosensitizer[b] | Do (rads)[c] | M.F. |
|---|---|---|
| Control | 420 ± 20 | |
| Menadione | 360 ± 20 | 1.17 |
| I (1c + 1d) | 320 ± 20 | 1.31 |
| II (1g + 1h) | 320 ± 20 | 1.31 |
| IV[d] | 300 ± 20 | 1.4 |

[a]Average value of at least three experiments, twelve mice in each experiment.
[b]Concentration of isoindole-4,7-diones 0.4 μg/g.
[c]Do obtained using doses from 200 to 1,400 rads at 200 rads intervals.
[d]See footnote c of Table IV.

The results of the tumor control dose fifty (TCD-50) are shown in Table III. The values of TCD-50 decrease as the concentration of the radiosensitizer increases. The dose modifying factors (D.M.F.) of 2.34, 2.43, and 2.53 at the maximum concentration (0.4 μg/g) of I, II and IV, respectively, are some of the highest reported thus far. These dose modifying factors are much higher than the 1.63 determined for menadione in the same system. The dose modifying factors also compare favorably with those reported for misonidazole, metronidazol, and other known chemical radiosensitizers.

Tumor Control Dose Experiments: Mice with transplanted soft tissue sarcoma were given different radiosensitizer doses dissolved in normal saline by intraperitoneal injection 30 minutes before irradiation. Tumors were measured twice a week during 120 days by determining the diameter with venier caliper in three dimensions. The tumor volume was computed according to the formula $V = 11/6 \times D_1 \times D_2 \times D_3$. Tumors were irradiated at a mean volume of 300 mm$^3$. All in vivo experiments were carried out at least three times with two control groups in each case. Each group has twelve mice. The results are given in Table IV.

TABLE IV

| TUMOR CONTROL DOSE[a,b] AND DOSE MODIFYING FACTOR | | | |
|---|---|---|---|
| Sensitizer Conc. | (μg/g) | TCD$_{50}$ (rads) | D.M.F. |
| Control | — | 6,200 ± 200 | — |
| Menadione | 0.4 | 3,800 ± 200 | 1.63 |
| I (1c + 1d) | 0.1 | 3,850 ± 200 | 1.61 |
| I (1c + 1d) | 0.2 | 3,350 ± 200 | 1.86 |
| I (1c + 1d) | 0.4 | 2,650 ± 150 | 2.34 |
| II (1g + 1h) | 0.1 | 3,700 ± 200 | 1.68 |
| II (1g + 1h) | 0.2 | 3,250 ± 200 | 1.91 |
| II (1g + 1h) | 0.4 | 2,550 ± 150 | 2.43 |
| IV[c] | 0.1 | 3,600 ± 200 | 1.72 |
| IV[c] | 0.2 | 3,000 ± 200 | 2.06 |
| IV[c] | 0.4 | 2,450 ± 150 | 2.53 |

[a]Average value of at least three experiments. Twelve mice in each experiment.
[b]Tumor Volume = 300 mm$^3$
[c]Mixture of 1,5-dimethyl and 1,6-dimethyl-2,3-trimethylene-2H—isoindole-4,7-diones.

The invention having been thus described, it will be appreciated that departures can be made therefrom within the scope of the claims which follow.

I claim:

1. An isoindoledione compound of the formula:

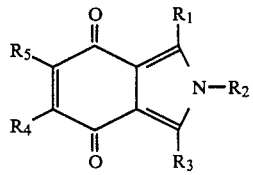

wherein:
R$_1$ and R$_3$ each separately is phenyl, substituted phenyl, alkyl of 1 to 4 carbons, —CHO, —CH$_2$OR$_6$, —CO$_2$R$_6$, —COR$_6$, hydrogen, or together with R$_2$ is a divalent alkyl or alkenyl group of 3 to 5 carbons which form a cyclic ring;
R$_2$ is phenyl, substituted phenyl, —CH$_2$OR$_6$, —CH$_2$CH$_2$OR$_6$, alkyl of 1 to 4 carbons or with either R$_1$ or R$_3$ is a divalent alkyl or alkenyl group of 3 to 5 carbons which form a cyclic ring;
R$_4$ and R$_5$ which may be the same or different each separately is hydrogen, alkyl of 1 to 4 carbons, —OR$_6$, —CO$_2$R$_6$, —COR$_6$, —CHO, —CH$_2$OR$_6$ or together R$_4$ and R$_5$ is a butadiene radical which forms a benzene ring;
R$_6$ is hydrogen or alkyl of 1 to 4 carbons; provided that R$_1$ and R$_3$ are not both phenyl and that when R$_4$ and R$_5$ are both hydrogen, R$_1$, R$_2$ and R$_3$ are not all methyl.

2. An isoindoledione compound according to claim 1 wherein
R$_1$ and R$_3$ are selected from phenyl, alkyl of 1 to 4 carbons, and together with R$_2$, R$_1$ or R$_3$ forms a cyclic ring;

R$_4$ and R$_5$ which may be the same or different are selected from hydrogen, alkyl of 1 to 4 carbons, and methoxy.

3. A compound according to claim 1 selected from the group consisting of:
1,2-dimethyl-3-phenyl-2H-benz[f]isoindole-4,9-dione;
1-phenyl-2,3-trimethylene-2H-benz[f]isoindole-4,9-dione;
1,2,5-trimethyl-3-phenyl-2H-isoindole-4,7-dione;
1,2,6-trimethyl-3-phenyl-2H-isoindole-4,7-dione;
5-methoxy-1,2,6-trimethyl-3-phenyl-2H-isoindole-4,7-dione;
6-methoxy-1,2,5-trimethyl-3-phenyl-2H-isoindole-4,7-dione;
5-methyl-1-phenyl-2,3-trimethylene-2H-isoindole-4,7-dione;
6-methyl-1-phenyl-2,3-trimethylene-2H-isoindole-4,7-dione;
5-methoxy-6-methyl-3-phenyl-1,2-trimethylene-2H-isoindole-4,7-dione;
6-methoxy-5-methyl-3-phenyl-1,2-trimethylene-2H-isoindole-4,7-dione;
1-methyl-2,3-trimethylene-2H-benz[f]isoindole-4,9-dione;
2-methyl-1-phenyl-2H-benz[f]isoindole-4,9-dione;
2,5-dimethyl-1-phenyl-2H-isoindole-4,7-dione;
2,6-dimethyl-1-phenyl-2H-isoindole-4,7-dione;
1,5-dimethyl-2,3-trimethylene-2H-isoindole-4,7-dione;
1,6-dimethyl-2,3-trimethylene-2H-isoindole-4,7-dione;
1-carboethoxy-5-methyl-2,3-trimethylene-2H-isoindole-4,7-dione;
1-carboethoxy-6-methyl-2,3-trimethylene-2H-isoindole-4,7-dione;
1-carboethoxy-2,5-dimethyl-3-phenyl-2H-isoindole-4,7-dione;
1-carboethoxy-2,6-dimethyl-3-phenyl-2H-isoindole-4,7-dione;
5-methyl-1,2-trimethylene-2H-isoindole-4,7-dione;
6-methyl-1,2-trimethylene-2H-isoindole-4,7-dione; and
1,2,3,5-tetramethyl-2H-isoindole-4,7-dione.

4. A method for the preparation of 2H-isoindoledione by the 1,3-dipolar addition of oxazolium-5-oxides to 1,4-quinones which comprises the steps of:
(a) generating, at a temperature of from about 20° to about 80° C. in the presence of a non-polar aprotic solvent and a dehydration agent, an oxazolium 5-oxide of the formula:

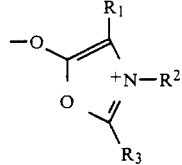

from an N-acyl amino acid of the formula

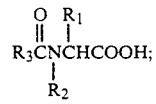

(b) reacting the oxazolium 5-oxide obtained in step (a) with a 1,4-quinone of the formula

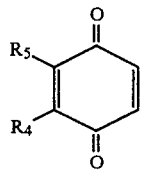

in the presence of a non-polar aprotic solvent for a period of time sufficient to produce a product of the formula

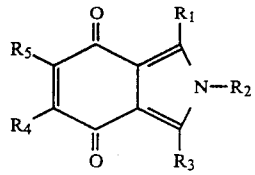

wherein:
R₁ and R₃ each separately is phenyl, substituted phenyl, alkyl of 1 to 4 carbons, —CHO, —CH₂OR₆, —CO₂R₆, —COR₆, hydrogen, or together with R₂ are a divalent alkyl or alkenyl group of 3 to 5 carbons which form a cyclic ring;
R₂ is phenyl, substituted phenyl, —CH₂OR₆, —CH₂CH₂OR₆, alkyl of 1 to 4 carbons or with either R₁ or R₃ is a divalent alkyl or alkenyl group of 3 to 5 carbons which form a cyclic ring;
R₄ and R₅ which may be the same or different is hydrogen, alkyl of 1 to 4 carbons, —OR₆, —CO₂R₆, —COR₆, —CHO, —CH₂OR₆ or together R₄ and R₅ are a butadiene radical which form a benzene ring;
R₆ is hydrogen or alkyl of 1 to 4 carbons; and
(c) separating and recovering the product from the solvent solution.

5. The method of claim 4 wherein the dehydration agent is acetic anhydride or dicyclohexylcarbodiimide.

6. The method of claim 4 wherein step (b) is carried out at a temperature ranging from about 20° to about 55° C.

7. The method of claim 4 or 5 wherein steps (a) and (b) are carried out in an inert atmosphere.

8. The method of claim 5 wherein said agent is acetic anhydride and prior to step (b) the reaction solution is neutralized by the addition of sodium carbonate and sodium sulfate.

9. The method of claim 4 wherein
R₁ and R₂ each separately is selected from the group consisting of phenyl, methyl
R₃ is methyl or phenyl;
R₄ is hydrogen, or methoxy; and
R₅ is hydrogen, or methyl.

10. The method of claim 4 wherein said 1,4-quinone is selected from the group consisting of 1,4-benzoquinone; 1,4-naphthoquinone; 2-methyl-1,4-benzoquinone and 2-methyl-3-methoxy-1,4-benzoquinone.

11. The method of claim 4 or 10 wherein said oxazolium 5-oxide is selected from the group consisting of 3-methyl-2,4-diphenyloxazolium-5-oxide; 2,3-dimethyl-4-phenyloxazolium-5-oxide and 2-phenyl-3,4-trimethyleneoxazolium-5-oxide.

12. A radiosensitizing composition for use in the radiotherapeutic treatment of cancerous tissues which comprises as an active ingredient an isoindoledione compound of the formula

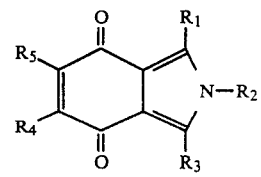

wherein:
R₁ and R₃ each separately is phenyl, substituted phenyl, alkyl of 1 to 4 carbons, —CHO, —CH₂OR₆, —CO₂R₆, —COR₆, hydrogen, or together with R₂ are a divalent alkyl or alkenyl group of 3 to 5 carbons which form a cyclic ring;
R₂ is phenyl, substituted phenyl, —CH₂OR₆, —CH₂CH₂OR₆, alkyl of 1 to 4 carbons or with either R₁ or R₃ is a divalent alkyl or alkenyl group of 3 to 5 carbons which form a cyclic ring;
R₄ and R₅ which may be the same or different is hydrogen, alkyl of 1 to 4 carbons, —OR₆, —CO₂R₆, —COR₆, —CHO, —CH₂OR₆ or together R₄ and R₅ are a butadiene radical which form a benzene ring;
R₆ is hydrogen or alkyl of 1 to 4 carbons; together with a pharmaceutically acceptable carrier.

13. An injectable composition according to claim 12, wherein said carrier is selected from the group consisting of sterile buffered saline solution and sterile water.

14. The composition of claim 12 in the form of a tablet, capsule, syrup or elixir.

15. A method for the radiotherapeutic treatment of cancerous tissues in mammals which comprises:
(a) administering to said mammal, in an amount effective to enhance subsequent radiation of cancerous tissue, a radiosensitizing composition as claimed in claim 12; and
(b) subsequently exposing the cancerous tissue to radiation whereby enhanced radiation of the tissue is achieved.

16. The method of claim 13 wherein the amount of said composition administered ranges from about 0.1 to 0.8 mg of active ingredient per kg body weight of the mammal.

17. The method of claim 16 wherein the amount of said composition administered is about 0.4 mg per kg of body weight.

18. The method of claim 12 wherein said radiation is gamma radiation.

19. The method of claim 12 wherein the time between steps (a) and (b) is from between about 15 to about 60 minutes.

* * * * *